US009315536B2

(12) United States Patent
Crea et al.

(10) Patent No.: US 9,315,536 B2
(45) Date of Patent: Apr. 19, 2016

(54) SELF-ASSEMBLING OLIGONUCLEOTIDES AND METHODS

(75) Inventors: Roberto Crea, San Mateo, CA (US); Guido Cappuccilli, San Mateo, CA (US)

(73) Assignee: Creatrone, Inc., Hillsborough, CA (US)

( * ) Notice: Subject to any disclaimer, the term of this patent is extended or adjusted under 35 U.S.C. 154(b) by 811 days.

(21) Appl. No.: 12/438,986

(22) PCT Filed: Aug. 29, 2007

(86) PCT No.: PCT/US2007/019036
§ 371 (c)(1),
(2), (4) Date: Jul. 27, 2009

(87) PCT Pub. No.: WO2008/027452
PCT Pub. Date: Mar. 6, 2008

(65) Prior Publication Data
US 2009/0299046 A1    Dec. 3, 2009

Related U.S. Application Data

(60) Provisional application No. 60/841,039, filed on Aug. 29, 2006.

(51) Int. Cl.
C12Q 1/68 (2006.01)
C07H 21/00 (2006.01)

(52) U.S. Cl.
CPC ..................................... C07H 21/00 (2013.01)

(58) Field of Classification Search
CPC ........ C12Q 1/68; C12Q 1/6876; C07H 21/00; C07H 21/02; C07H 21/04
USPC .......... 435/6.1; 536/22.1, 23.1, 24.3
See application file for complete search history.

(56) References Cited

U.S. PATENT DOCUMENTS

| | | | |
|---|---|---|---|
| 4,988,167 A * | 1/1991 | Fergason ........................ 349/195 |
| 5,521,289 A | 5/1996 | Hainfeld et al. | |
| 5,695,937 A * | 12/1997 | Kinzler et al. ................ 435/6.12 |
| 5,780,613 A * | 7/1998 | Letsinger et al. ........... 536/25.33 |
| 5,824,475 A | 10/1998 | Nelson et al. | |
| 6,294,372 B1 * | 9/2001 | Burian et al. ............. 435/252.33 |
| 6,369,206 B1 | 4/2002 | Leone et al. | |
| 6,432,641 B1 | 8/2002 | Lee et al. | |
| 6,645,721 B2 | 11/2003 | Mirkin et al. | |
| 6,733,975 B2 | 5/2004 | Sato et al. | |
| 6,958,216 B2 * | 10/2005 | Kelley et al. ........................ 506/39 |
| 6,974,703 B2 | 12/2005 | Mauze et al. | |
| 2001/0053519 A1 * | 12/2001 | Fodor et al. ......................... 435/6 |
| 2002/0012913 A1 * | 1/2002 | Gunderson et al. ................ 435/6 |
| 2002/0016306 A1 | 2/2002 | Hutchison et al. | |
| 2002/0187476 A1 * | 12/2002 | Koroulis et al. ................... 435/6 |
| 2002/0192649 A1 * | 12/2002 | Lizardi ............................... 435/6 |
| 2004/0248115 A1 * | 12/2004 | Fujii ................................... 435/6 |
| 2005/0112614 A1 * | 5/2005 | Cook et al. ......................... 435/6 |
| 2005/0130180 A1 | 6/2005 | Luo et al. | |
| 2006/0154380 A1 | 7/2006 | Egusa et al. | |
| 2008/0045473 A1 * | 2/2008 | Uhlmann et al. ................ 514/44 |
| 2008/0167454 A1 * | 7/2008 | Luo et al. ..................... 536/23.1 |
| 2009/0299046 A1 * | 12/2009 | Crea et al. .................... 536/25.3 |
| 2010/0311126 A1 * | 12/2010 | Gibson et al. ................ 435/91.2 |
| 2012/0041184 A1 * | 2/2012 | Beigelman et al. .......... 536/24.5 |

FOREIGN PATENT DOCUMENTS

| | | |
|---|---|---|
| EP | 1304386 A1 * | 4/2003 |
| EP | 1880019 A1 | 1/2008 |
| WO | WO 2006/124089 A1 | 11/2006 |
| WO | WO2008027452 A2 | 3/2008 |

OTHER PUBLICATIONS

Sarkar et al, .Nucleic Acids Research 33(1) :143 (2005).*
Adereth et al.,Site-directed Mutagemnesis using Pfu DNA polymerase and T4 DNA ligase. Biotechniques 38 (6) : 864 (2005).*
Chen et al.,Total Gene Synthesis: Novel Single-Step and Convergent Strategies Applied to the Construction of a 779 Base Pair Bacteriorhodopsin Gene. JACS 116 : 8799 (1994).*
Crameri et al., DNA shuffling of a family of genes from diverse species accelerates directed evolution. Nature 391 : 288 (1998).*
Goeddel et al., Expression in *Escherichia coli* of chemically synthesized genes for human insulin. PNAS 76(1) : 106 (1979).*
Itakura et al., Expression in *Escherichia coli* of a chemically synthesized gene for the hormone somatostatin. Science 198 :1056 (1977).*
Stemmer , DNA shuffling by random fragmentation and reassembly: in vitro recombination for molecular evolution. PNAS 91 :10747 (1994).*
Stemmer et al., Single-step assembly of a gene and entire plasmid from large numbers of oligodeoxyribonucleotides. Gene 164 :49 (1995).*
Stemmer , Rapid evolution of a protein in vitro by DNA shuffling. Nature 370 : 389 (1994).*
Stewart et al. , A quantitative assay for assessing allelic proportions by iterative gap ligation. Nucleic Acids Research 26(4) : 961 (1998).*
Rouwendal et al., Simultaneous mutagenesis of multiple sites: application of the ligase chain reaction using PCR products instead of oligonucleotides. Biotechniques 15 (1) : 68 (1993).*
Porath et ah. et al. Direct Measurement of electrical transport through DNA molecules. Nature 403 : 635 (2000).*
Phosphorylation of Oligonucleotides Thermo Electron Corp. Techical Information TI-OL 10805 (2005).*
Dirks et al. Triggered amplification by hybridization chain reaction [PNAS 101 (43) : 15275 (2004)].*
Evanko D. Hybridization chain reaction [Nature Methods 1 (3) : 186 (2004)].*
Li et al., Chemical self-replication of palindromic duplex DNA. Nature 369 : 218 (1994).*
Furrer et al.,Opposite Effect of Counterions on the Persistence Length of Nicked and Non-nicked DNA. Journal of Molecular Biology 266 : 711 (1997).*
Sarkar et al., Condensation of oligonucleotides assembled into nicked and gapped duplexes: potential structures for oligonucleotide delivery. Nucleic Acidfs Research 33(1) :143 (2005).*
Lowe et al, A computer program for selection of oligonucleotide primers for selection of oligonucleotide primers for polymerase chain reaction. Nucleic Acids Research 18 (7) :1757 (1990).*

(Continued)

Primary Examiner — Ethan C Whisenant
(74) Attorney, Agent, or Firm — Carr & Ferrell LLP

(57) ABSTRACT

A composition comprising individual single-stranded oligonucleotides capable of self assembling to form a pair of complementary, substantially contiguous single strands of a double-stranded nucleic acid filament, and a method for forming such filaments are disclosed.

6 Claims, 4 Drawing Sheets

(56) References Cited

OTHER PUBLICATIONS

Akasaka, T. et al., "Transformation from block-type to graft-type oligonucleotide-glycopolymer conjugates by self-organization with half-sliding complementary oligonucleotides and their lectin recognition", 12:776-785 (2001).
Bhalla, V. et al., "DNA electronics", *EMBO Reports*, 4(5):442-445 (2003).
Braun, E. et al., "DNA-templated assembly and electrode attachment of a conducting silver wire", *Nature*, 391(6669):775-778 (1998).
Fink, H.W. and Shoneberger, C., "Electrical Conduction through DNA Molecules", *Nature*, 398(6726):407-410 (1999).
Guo, P., "RNA nanotechnology: engineering, assembly and applications in detection, gene delivery and therapy" *Journal of Nanoscience and Nanotechnology*, 5(12):1964-1982 (1975).
Richter, J et al., "Construction of highly conductive nanowires on a DNA template", *Appl Phys Letters*, 78(4):536-538 (2001).
International Search Report and Written Opinion for PCT application PCT/US2007/019036, Mar. 17, 2008 14 pages (2008).
Sarkar, T., et al.,"Dietary Polyunsaturated Fatty Acids and Cancers of the Breast and Colorectum: Emerging Evidence for Their Role as Risk Modifiers", *Nucleic Acids Research*, 33(1):1430151 (2005).
International Search Report for PCT Application PCT/US2007/019036 dated Mar. 17, 2008.
Hainfeld, J., F. et al., "DNA nanowires." Microscopy and Microanalysis7 (NY, NY) (2001). pp. 1034-1035; available at: http://www.nanoprobes.com/applications/MSADNA01.html.
Pevzner, "1-Tuple DNA sequencing: computer analysis." Journal of Biomolecular Structure & Dynamics 7 (1):063 (1989) (Abstract only—full article not available).

* cited by examiner

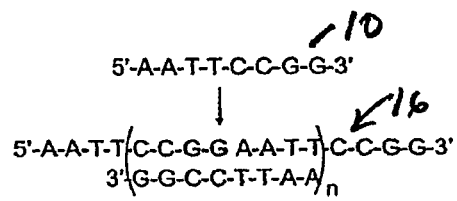
Fig. 3A
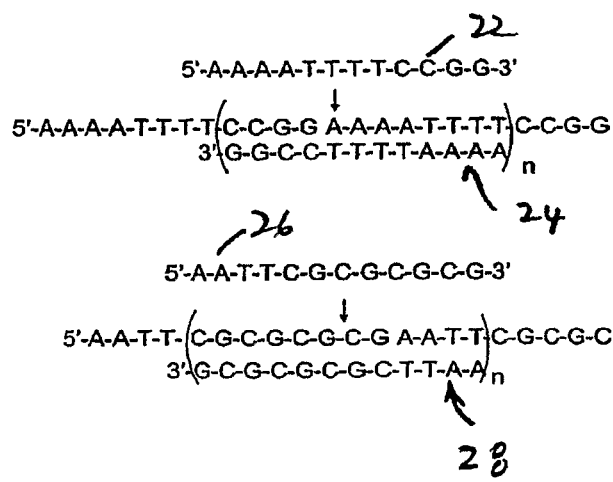
Fig. 3B
Fig. 3C
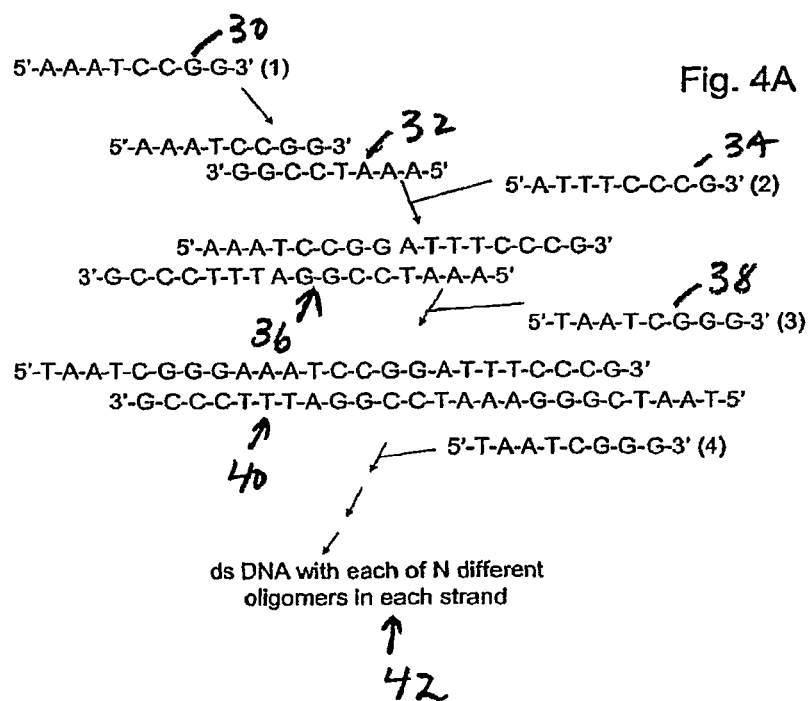
Fig. 4A

SEQUENCE LISTING

```
<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aattccggaa ttccgg                                                      16

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaattttcc gg                                                          12

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaattttcc ggaaaatttt ccgg                                             24

<210> SEQ ID NO 4
<211> LENGTH: 12
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 4
aattcgcgcg cg                                                           12

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aattcgcgcg cgaattcgcg cgcg                                              24

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaatccggat ttcccg                                                       16

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taatcgggaa atccggattt cccg                                              24

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaattcccgg                                                              10

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aatttccgga aatcccgg                                                     19

<210> SEQ ID NO 10
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
aaatttccgg g                                                            11

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaatttccgg gaaattcccg g                                                 21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaatttccgg gaatttcccg g                                                 21

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaatttcccg gg                                                           12

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccggaattcc ggaatt                                                       16
```

SELF-ASSEMBLING OLIGONUCLEOTIDES AND METHODS

This application is the National Stage of International Application No. PCT/US2007/019036 filed on Aug. 29, 2007, which claims the benefit of U.S. Provisional Application No. 60/841,039 filed on Aug. 29, 2006, both of which are incorporated herein by reference in their entirety.

FIELD OF THE INVENTION

The present invention relates to self-assembling oligonucleotides and methods of their use, e.g., in micro- and nano-fabrication.

REFERENCES

Braun, E. et al., Nature (London) 391, 775 (1998).
Richter, J. et al., Appl. Phys. Lett. 78, 536 (2001).
Hainfeld, J. F. et al. Microsc. Microanal., 7, 1034 (2001).
Bhalla, V. et al. EMBO Reports, Vol. 4, No. 5, 442-445 (2003).
Fink, H. W. and Shonenberger, C. Nature, Vol. 398, 407-410 (1999).

BACKGROUND OF THE INVENTION

Under existing silicon-based computer chip technology, the number of transistors on a chip has doubled about every 18 months according to Moore's law. This pace is likely to slow considerably because of physical and atomic constraints on silicon chips. For instance, the wire components used in silicon chips cannot be made smaller than 300 nm due to the wavelength of light used in lithography. (Hainfeld, 2001). Enlarging silicon computer chips will accommodate greater processing power. Yet in personal computing applications, silicon chips can only be enlarged so much, especially in the context of laptop computers. Additionally, there is a need to for small powerful chips to be used in cellular phones, PDAs, and other handheld devices. Transistors can be made smaller if they are made from nanowires having a diameter of less than 10 nm. Use of these smaller transistors could dramatically increase the number of transistors per area of the chip, allowing computer chips to become smaller and more powerful.

DNA may be used create nanowires because it is sufficiently small and can be made or fashioned as elongate filaments. Double-stranded DNA has a width of approximately 2 nm and each base pair adds approximately 0.34 nm in length to the molecule. Recently, double-stranded DNA has been shown to conduct electricity. (Porath et al. 2000) The conductive ability of DNA may be as good as that of a semiconductor. (Fink and Shonenberger, 1999).

Further, the conductivity of a DNA strand may be enhanced in a variety of ways. In one approach, the filament is doped with metal ions, such as Zn, Co, Ni. With sufficient doping, the conductivity of the filament may be enhanced several orders of magnitude. Alternatively, nucleic acid filaments may be coated with a conductive film, such as a gold or silver film applied by metal atom deposition of other coating methods (Braun 1998 and Richter 2001). Another exemplary DNA nanowire may be created by binding gold to a DNA filament. (Hainfeld, 2001) This is further described in US Patent Publications 2006/0154380 and 2002/0016306, which are hereby incorporated by reference. DNA filaments may be connected to other circuit elements by hybridization with a single-stranded DNA sequence, using standard DNA splicing and ligation methods. (Hainfeld, 2001). Other circuit elements include other DNA nanowires or solid-state circuit elements that are covalently bound to a single-stranded DNA molecule.

Each DNA strand that comprises a nanowire may be made using a commercially available polynucleotide synthesizer, yet this approach is suboptimal. The maximum length of a DNA that can be feasibly made using this technique is 100 base pairs. Furthermore, DNA synthesizers will contain shorter DNA strands as impurities. Alternatively, the DNA used to make a nanowire can be assembled from smaller pure oligonucleotides.

It would therefore be desirable to provide oligonucleotides that can be easily synthesized in bulk and which can be assembled readily into desired lengths and/or filament bundles.

SUMMARY OF THE INVENTION

In one aspect, the invention includes a composition of individual single-stranded oligonucleotides capable of self-assembly. Each oligonucleotide is composed of two adjacent segments that can hybridize to the same segment in another oligonucleotide molecule of the composition. Under hybridization conditions, the oligonucleotides will self assemble to form a double-stranded polynucleotide in which the first and second segments of an oligonucleotide in one strand of the filament are hybridized with complementary first and second segments, respectively, of two adjacent oligonucleotides in the second strand of the filament, where each strand is composed of a plurality of said oligonucleotides.

The first and second segments in the single-stranded oligonucleotides may be the same or different lengths and may be palindromic and/or self-complementary. The oligonucleotides may have a phosphate group at their 5'-ends to allow the 5' end of one oligonucleotide to be ligated to the 3' end of an adjacent polynucleotide on the same strand, thus to form double-stranded filaments with integral strands.

The individual molecules may each contain between 1-3 nucleotide bases between the first and second segments, such that each substantially contiguous strand in the double stranded filament contains periodic gaps that are 1-3 bases in length and offset from gaps in the other strand in the filament.

The first segment of the oligonucleotides may be composed substantially of A and T bases only, and the second segment, of substantially of G and C bases only, such that the double stranded filament has regions composed substantially of paired A and T bases only alternating with regions of paired G and C bases only.

For use in forming a double-stranded DNA having a selected length, the oligonucleotides may include a plurality of N sets of different-sequence, but same-length oligonucleotides, where the 5'-end sequence in each set of oligonucleotides is complementary to the 5'-end sequence in only one other set of oligonucleotides, and where the 3'-end sequence in each set of oligonucleotides is complementary to 3'-end sequence in only one other set of oligonucleotides. In this embodiment, the pair of complementary, substantially contiguous single strands of a double-stranded nucleic acid filament is composed of only one oligonucleotide from each of the N sets of oligonucleotides.

Alternatively, for use in forming a double-stranded DNA having a selected length, the oligonucleotides may include a plurality of N sets of different-sequence, different-length oligonucleotides, where the 5'-end sequence in each set of oligonucleotides is the same length as and complementary to the 5'-end sequence in only one other set of oligonucleotides, and where the 3'-end sequence in each set of oligonucleotides is the same length as and complementary to 3'-end sequence in only one other set of oligonucleotides. The pair of complementary, substantially contiguous single strands of a double-stranded nucleic acid filament is composed of only one oligonucleotide from each of the N sets of oligonucleotides.

In another aspect, the invention includes a method for forming a double-stranded duplex nucleic acid filament, by reacting in solution, under nucleic acid-acid hybridization conditions, the oligonucleotides described above.

The method may further include ligating adjacent ends of the oligonucleotides forming each strand of the double-stranded filament, where the oligonucleotides each have a 5'-end phosphate group, and the ligating is carried out with a ligase enzyme in the presence of ATP.

Where the method is employed to produce a double-stranded duplex nucleic acid filament of a defined length, the individual oligonucleotides may include (i) include a plurality of N sets of different-sequence, but same-length oligonucleotides, where the 5'-end sequence in each set of oligonucleotides is complementary to the 5'-end sequence in only one other set of oligonucleotides, and where the 3'-end sequence in each set of oligonucleotides is complementary to 3'-end sequence in only one other set of oligonucleotides, or (ii) a plurality of N sets of different-sequence, different-length oligonucleotides, where the 5'-end sequence in each set of oligonucleotides is the same length as and complementary to the 5'-end sequence in only one other set of oligonucleotides, and where the 3'-end sequence in each set of oligonucleotides is the same length as and complementary to 3'-end sequence in only one other set of oligonucleotides.

For use in forming a bundle of sequence-aligned double-stranded nucleic acid filaments, the oligonucleotide self-assembly step may be carried out in the presence of a selected-length double-stranded template filament having a sequence formed by self-assembly of such oligonucleotides, wherein the template filament directs the assembly of the oligonucleotides to form a bundle of sequence-aligned double-stranded nucleic acid filaments.

For use in producing a double-stranded duplex nucleic acid filament bridging a pair of selected regions on a substrate, the method may involve the step of (a) anchoring at each region on the substrate, a single-stranded nucleic acid fragment whose sequence is complementary to one segment of the oligonucleotides, (b) exposing the substrate and anchored single-stranded nucleic acid fragments to a solution of the oligonucleotides, under nucleic acid hybridization conditions, and (c) by this exposing, forming between the two regions, and connected therewith, a double-stranded nucleic acid filament composed of overlapping oligonucleotides.

Each region of the solid support may be a gold film electrode, and the fragments may be attached to the film through a disulfide linkage between a surface-bound thiol reagent and a phosphorothio group at the 3'-end of the fragment.

For use in creating an electrically conductive filament between the first and second regions, the double-stranded nucleic acid filament formed in step (c) may be coated with an electrically conductive film, or may be treated with a solution of a Zn, Co, or Ni salt, under conditions effective to incorporate Zn, Co, or Ni atoms between the filament's nucleic acid bases.

These and other objects and features of the present invention will become more fully apparent when the following detailed description is read in conjunction with the accompanying drawings.

BRIEF DESCRIPTION OF THE DRAWINGS

FIG. 3A shows a scheme of making a polynucleotide using a single oligonucleotide that has palindromic sequence at the 5'-end of length equal to that of the palindromic sequence at the 3'-end.

FIGS. 3B-3C shows a scheme for making a polynucleotide using a single oligonucleotide that has sequence at the 5'-end of length different from the sequence at the 3'-end.

FIG. 4A shows a scheme for making a polynucleotide of a specific length using multiple oligonucleotides of equal length with sequences at the 5'-end and the 3'-end. The length is specifically determined because the growing double-stranded polynucleotide will hybridize with only one other polynucleotide in each step.

DETAILED DESCRIPTION OF THE INVENTION

I. Definitions

Figure 1:
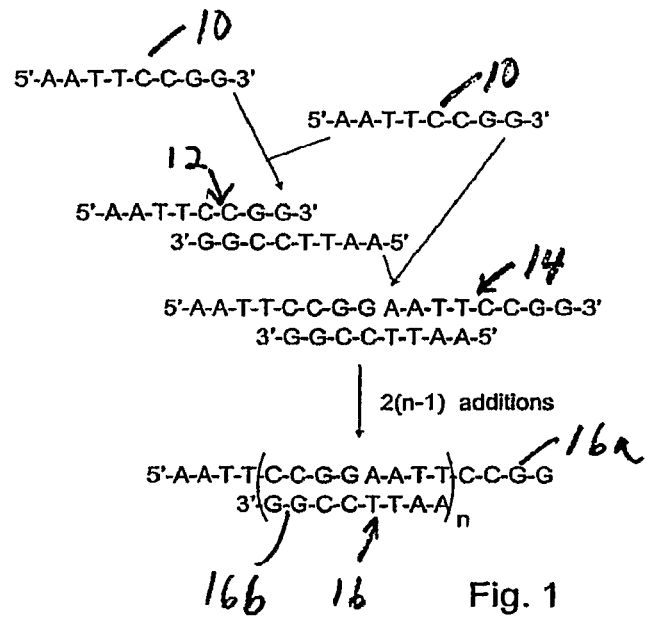
FIG. 1 shows steps for hybridizing oligonucleotides with 5' and 3' palindromic sequences to make a double-stranded polynucleotide.

The terms below have the following definitions unless indicated otherwise.

"Oligonucleotide" means a natural nucleic acid, typically in single-stranded form, such as DNA or RNA, or a nucleic acid analog, having either non-ribose subunits, e.g., morpholino subunits, or charged or uncharged backbone linkages other than natural phosphodiester linkages, e.g., phosphorothioate, phosphoroamidate, phosphorodiamidate, and the like. An "oligonucleotide" has a sequence of bases that allows it to hybridize, under suitable hybridization conditions, with a complementary sequence in another oligonucleotide via Watson-Crick base pairing. Oligonucleotides are typically less than 100 bases in length, typically 8-30 bases. The terms DNA, nucleic acid, including RNA, and nucleic acid analogs are used interchangeably.

A "palindromic sequence" is a DNA locus whose 5'-to-3' sequence is identical on each DNA strand. The sequence is the same when one strand is read left to right and the other strand is read right to left.

A double-strand filament is an oligonucleotide or polynucleotide filament having a length of from less than 100 bases (oligonucleotide strands) to a length of up to several hundred or several thousand bases (polynucleotide strands), and formed of complementary or substantially complementary strands, where each strand is formed of ligated or unligated side-by-side oligonucleotides, and each oligonucleotide in one strand is hybridized with portions or segments of two adjacent oligonucleotides on a second strand.

An oligonucleotide strand in a double-stranded nucleic acid filament is "substantially contiguous" if the confronting tail-to-head nucleotide bases in adjacent oligonucleotides forming the strand are immediately adjacent, or are spaced at most by 1-3 bases.

II. Oligonucleotide Composition and Self-Assembly

The invention includes, in one aspect, individual oligonucleotides that can self-assemble under hybridizing conditions, to form a double-stranded oligonucleotide or polynucleotide filament. Each oligonucleotide includes a 5'-end segment or sequence and a 3'-end segment or sequence. Each segment of an oligonucleotide is capable of hybridizing with the corresponding 5'-end or 3'-end segment of at least one other oligonucleotide in the composition. Although the invention is illustrated with respect to oligonucleotides whose end segments are composed exclusively of pyrimidine bases (A or T or U) or purine bases (G or C), either or both regions may contain mixtures or both base types, as long as the sequences allow for self-assembly by hybridization, as described herein.

A. Compositions with Single Oligonucleotide Sequences

This section describes an embodiment in which the individual oligonucleotides in a self-assembly composition are identical, that is, the composition includes a single oligonucleotide species, and each individual oligonucleotide (oligonucleotide molecule) has the same sequence and length. As will be seen, this embodiment has advantages of simplicity and cost, but the self-assembly reaction with a single oligonucleotide species may be more difficult to control, for example, to achieve desired length filaments.

The oligonucleotides in this embodiment are capable of self-assembling to form "open-ended" double-stranded nucleic acid filaments, according to the self-assembly scheme illustrated in FIG. 1. The figure shows an 8-mer oligonucleotide 10 having a 5'-end palindromic segment AATT, and a 3'-end palindromic segment CCGG. As seen in the figure, two such oligonucleotides are capable of forming, under hybridization conditions, a double-stranded complex 12 in which the two 3'-end segments are hybridized by Watson-Crick, and the two adjacent 5'-end segment are single-stranded overhangs. The overhangs, in turn, can now hybridize with the same oligonucleotides in solution, to form increasingly longer double-stranded complexes, such as complex 14 formed after 2 oligonucleotide additions, where each two oligonucleotide additions add one oligonucleotide to each strand of the complex. Thus, after 2n–1 additions, the double-stranded complex shown at 16 is formed that has a pair of complementary, substantially contiguous single strands, indicated at 16a, 16b, in which the first and second segments of an oligonucleotide in one strand of the filament are hybridized with complementary first and second segments, respectively, of two adjacent oligonucleotides in the second strand of the filament, and each strand is composed of n such oligonucleotides.

That is, the filament shown in FIG. 1 has a pair of hybridized double stranded lengths corresponding to n repeats of the sequence in each oligonucleotide, and two overhangs that together make up the sequence of a single oligonucleotide. Although the two overhangs are shown on the same strand, addition of a single oligonucleotide to the filament would of course place one overhang on each strand.

It will be appreciated that during the self-assembly reaction, many double-stranded filament complexes are being formed, and these may have a range of filament lengths. The self-assembly reaction may be terminated, at a desired end point, e.g., desired average filament length, by controlling the concentration of oligonucleotide in the reaction, and/or changing the reaction conditions, e.g., by cooling, to block further hybridization. More generally, the "length" of the filament is dictated by the (a) concentration of the oligonucleotides in the reaction, (b) the sequence (G/C rich vs. A/T rich), (c) the number of self associating bases (pairing) and (d) the conditions under which self associating event occurs. Conditions may include: (1) solvents/buffers, (2) temperature of the self assembly solution, (3) presence of "ligating" enzymes, (4) "chain terminating" DNA units (see below), (5) presence of additional chemistry at the 3'-5' gap to favor the passage of electrons/electricity, and (6) the use of substrates/templates/devices, which act as mold for the alignment and ordered stacking of DNA polymers.

Chain terminators are DNA sequences designed to stop the self assembling process of palindromic sequences by competing with the self assembly process. These units lack the second palindromic unit, therefore can only occur once for each chain elongation. Chain terminators may be useful to stop the self assembly process to a desirable number of events, so that a more homogeneous family of polymers is generated. The effect of chain termination by these DNA molecules can be monitored by adding them to the above reactions. Concentration of chain terminators and time of addition to the self annealing reactions will be monitored. Chain terminating DNA units may be useful as anchoring moieties. For example, the presence of a cross linking chemical at the 5'-end of these units will favor the use of DNA polymers in conjunction with activated solid surfaces. Biotin-bearing DNA terminators can be used to link the DNA polymers to avidin coated surfaces, etc.

Ideally, for bio-circuits applications, homogeneous polymerization will be achieved so that filaments of self associating DNA are obtained with similar length and folding characteristics. It will be desirable to produce DNA filaments of similar shape and length to construct biotransistors and other "information" devices. Compositions designed to form specified filament lengths are described further below.

In one embodiment, the individual oligonucleotides each contain between 1-3 nucleotide bases between said first and second segments. As can be appreciated, when the oligonucleotides in this embodiment self assemble, each of the resulting strands forming the double-stranded filament contains periodic gaps that are 1-3 bases in length and offset from gaps in the other strand in the filament. These gaps may be used, for example, to insert metal ions or atoms or other groups capable of modifying the electronic properties of the strands. Alternatively, filaments with such 1-3 based gaps can be enzymatically modified to fill in and ligate the gaps, forming filaments in which each strand is continuous and integral.

In another embodiment, and the one illustrated herein, the first segment of the oligonucleotides is composed substantially of A and T bases only, and the second segment of the oligonucleotides is composed of substantially of G and C bases only, yielding a double stranded filament has regions composed substantially of paired A and T bases only alternating with regions of paired G and C bases only. This arrangement of alternating regions of A:T and G:C confers selected electronic properties on the filaments, due to the different donor:acceptor nature of the two regions.

Figure 2:
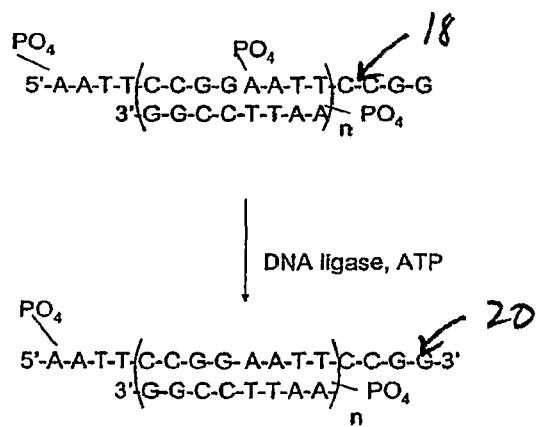
FIG. 2 shows addition of phosphate groups at the 5' end of the oligonucleotides so that ligation can occur without the need for treating the oligonucleotides with a kinase before reaction.

Following the self-assembly reaction illustrated with respect to FIG. 1, the two strands of a filament may be individually ligated to form continuous covalently linked strands without breaks between adjacent oligonucleotides. This may be done, as illustrated in FIG. 2, by providing the oligonucleotides with 5'-end phosphate groups, according to standard oligonucleotide synthesis methods. The double-stranded filament formed by self-assembly will then have 5'-end phosphate groups spaced at even intervals along the length of each strand shown at 18 in FIG. 2. By reacting the resulting filament with a ligase enzyme, e.g., T4 ligase, in the presence of ATP and under suitable ligation conditions, both strands are internally linked to produce the continuous-strand complex shown at 20 in FIG. 2. Following ligation, the double-stranded complexes may be fractionated, e.g., by gel electrophoresis, to yield fragments of desired lengths.

In the embodiments illustrated above, all of the oligonucleotides have the same 5'-end and 3'-end region sequence and length, as noted, and both regions are palindromic, that is, have the same sequence when read from 5'-to-3' in one strand and from 3'-to-5' in the opposite strand. Both of these segments or regions are illustrated as 4-base segments. Typically, however, the oligonucleotide segments will be longer, e.g., 6-15 bases of longer, to provide greater thermal stability at a suitable reaction temperature, e.g., room temperature or greater. Further, the percentage of A:T/G:C may be varied according to known method to achieve a desired duplex stability.

FIGS. 3A-3C show various oligonucleotides having different A:T/G:C ratios and/or different palindromic sequences. The oligonucleotide 10 in FIG. 3A is the same as that shown in FIGS. 1 and 2, and produces the double-stranded filament shown at 16. Oligonucleotide 22 in FIG. 3B, representing an oligonucleotide useful in constructing an A:T rich filament, contains an 8-base 5'-end A-A-A-A-T-T-T-T segment and a 4-base C-C-G-G segment, resulting in a double-stranded filament 24 having a 12-base double-stranded repeat sequence and an 8-base and 4-base overhang. Oligonucleotide 26 in FIG. 3C, representing an oligonucleotide useful in constructing a GUCCI rich filament, contains a four-base 5'-end A-A-T-T segment and an 8-base G-C-G-C-G-C-G-C segment, resulting in a double-stranded filament 28 having a double-stranded 12-base repeat and an 4-base and 8-base overhang. The ratios, lengths and sequences of AT and GUCCI regions may be adjusted to achieve desired electronic, e.g., semiconductor properties in the filaments, as discussed below.

B. Compositions with Multiple Oligonucleotide Sequences

This section describes a composition of the invention having N different sequence and/or different length oligonucleotide species. As will be seen, the compositions are designed for self-assembly of filaments having a defined length and sequence, and typically form filaments containing in each strand, one of each of the N different-sequence or different-length oligonucleotides.

The embodiment illustrated in FIG. 4A contains a plurality (N) of different-sequence, but same-length oligonucleotide species, three of which are indicated at 30, 34, and 38 in FIG. 4A. In this embodiment, one of the 5'-end or 3'-end segments of a given oligonucleotide species is complementary to the corresponding 5'-end or 3'-end segment of one other oligonucleotide species in the composition, and the other of the two segments is complementary to the corresponding segment of a third oligonucleotide species in the composition. In addition, at least one of the species may have a self-complementary sequence that allows for initial oligonucleotide hybridization.

For example, oligonucleotide 30 in the composition has a palindromic 3'-end G-G-C-C sequence that allows the oligonucleotide to form a duplex dimer 32. However, since the 5'-end regions of this oligonucleotide are not complementary, self assembly by that oligonucleotide alone ends. A second oligonucleotide species 34 in the composition has a 5'-end segment that is complementary to the 5'-end segment of oligonucleotide 30, allowing this species to hybridize to both strands of complex 32, through the 5'-end segment overhangs, to form complex 36 that is expanded bi-directionally. Similarly, a third species 38 having a 3'-end segment that is complementary to the overhang 3'-end segments of the complex 36, allowing this species to hybridize to both strands of complex 36, through the 3'-end segment overhangs to form complex 40, again by bi-directional expansion.

After each hybridization step, the pattern described in the second and third hybridization steps continues. The fifth, seventh and additional odd-numbered oligonucleotides must have a 3' segment that is the reverse compliment of the 3' segment of the fourth, sixth and previous even-numbered oligonucleotide. Furthermore, the sixth, eighth, and additional even-numbered oligonucleotides must have a 5' segment that is the reverse compliment of the 5' segment of the fifth, seventh, and previous odd-numbered oligonucleotides. Bidirectional growth continues in this manner until all N different-sequence species are incorporated into each of the two filament strands, as indicated at 42 in the figure.

Although only one of the oligonucleotide species described above has a self-complementary segment (oligonucleotide 30), it will be appreciated that other species may also have a self-complementary segment, since the stability of any two-oligonucleotide hybrids, where only one of the two segments are hybridized, would be substantially less than the stability of the same species in a growing strand, where both segments would be hybridized, and the species would therefore tend to participate preferentially in filament formation.

Figure 4B:
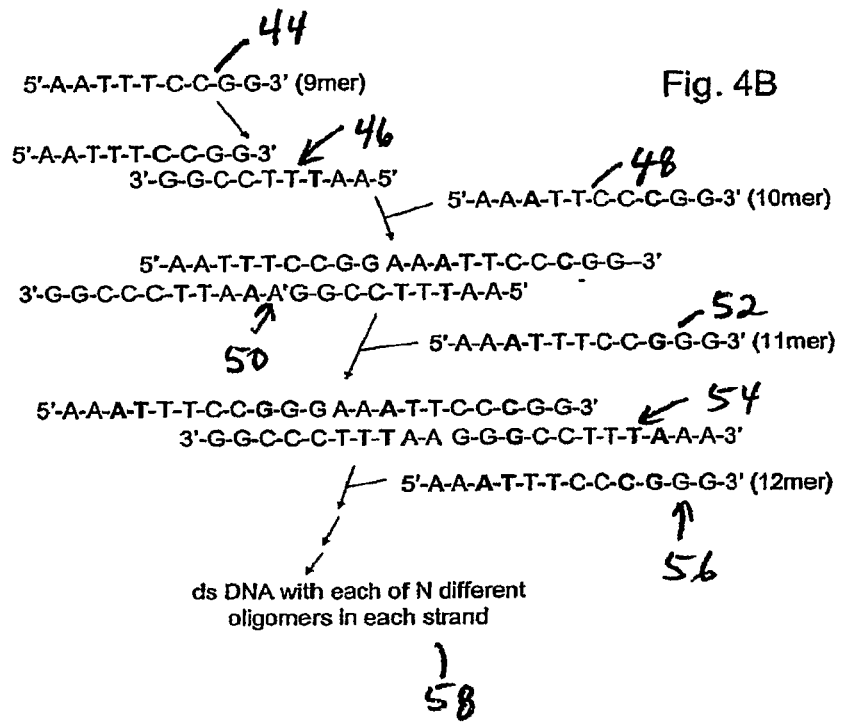
FIG. 4B shows a scheme for making a polynucleotide of a specific length using multiple oligonucleotides with sequences at the 5'-end and the 3'-end. In the hybridization, each successive oligonucleotide that hybridizes to the growing double-stranded polynucleotide is one base pair longer than the preceding oligonucleotide. The length is specifically determined because the growing double-stranded polynucleotide will hybridize with only one other polynucleotide in each step.

In another embodiment, illustrated in FIG. 4B, the composition of the invention includes N different-sequence and different length species, but where, as above, even- or odd-numbered species have 5'-end or 3'-end segments that are complementary to the 5'-end or 3'-end segments of odd- or even numbered species, respectively. As illustrated, an "initial" species 44 has a self-complementary 3'-end region G-G-C-C capable of forming duplex hybrids, with non-self-complementary 5'-end T-T-T-A-A segments. A second species 48 has a 5'-end segment A-A-A-T-T that is complementary to the two overhangs in complex 46, to form complex 50 by bi-directional expansion by one oligo. A third species 52 has a 3'-end segment C-C-G-G-G segment that is complementary to the two overhangs in complex 50, to form complex 54, which then expands by addition of species 56, and so forth, as above, until a duplex filament 58 having N different-sequence, different-length oligonucleotides in each strand is formed. Thus, the final length of the filaments formed is uniform and equal to the combined lengths of each of the N oligonucleotide species.

III. Construction of a Nucleotide-Based Nanowire

Figure 5:
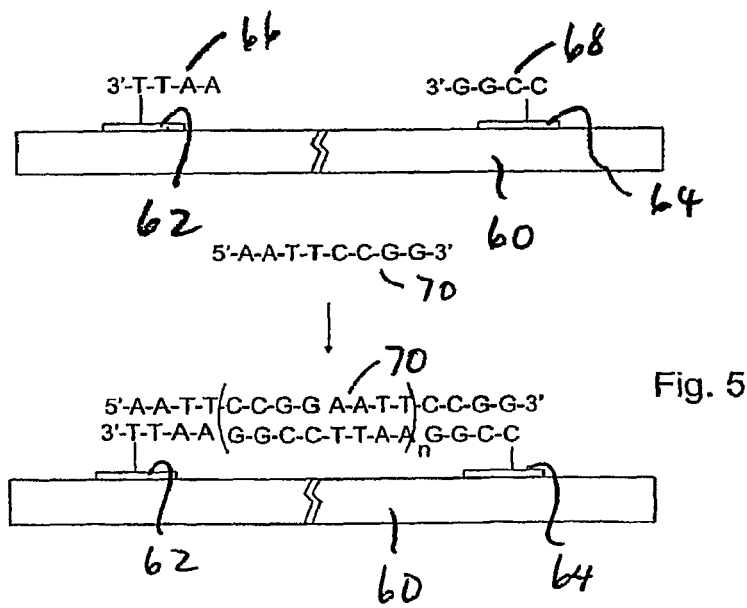
FIG. 5 shows the synthesis of a double-stranded polynucleotide connected to a solid support. The oligonucleotide used to make the polynucleotide can hybridize to the single-stranded oligonucleotides that are chemically bound to the solid support.

In one aspect, the filaments formed by self-assembly, as above, may be used in forming patterned-wire nanostructures, such as wires, in a micro- or nano-fabrication method, as illustrated in FIG. 5. The figure shows a microfabrication substrate 60 having two spaced regions, 62, 64, such as electrode regions. Each region has attached to its surface, one or more oligonucleotides, such as oligonucleotide 66 on region 62 and oligonucleotide 68 on region 64. The substrate regions may carry an electrically conductive film formed of gold, silver, or the like. The oligonucleotides may be attached to a gold film through thiol linkages or a disulfide linkage between a surface-bound thiol reagent and a phosphorothio group at the 3' end of the oligo, as described, for example, in U.S. Pat. Nos. 6,369,206; 5,521,289; 6,369,206; 6,645,721; and 6,733,975, all of which are incorporated herein by reference. The bound oligonucleotides are complementary to the overhangs in a double-stranded filament, such as filament 70 similar to filament shown at 16 in FIG. 1.

To form the filament connection between the two regions, the region is exposed to a solution of the oligonucleotides, under suitable hybridization conditions, allowing both anchorages of the oligonucleotides to the attached oligonucleotides, and self-assembly to form filament connections, such as connection 70, across the two regions.

Where it is desired to form the shortest connection between a pair of anchor regions, e.g., substantially straight lines, the self-assembly composition may include N different-length and/or different-sequence oligonucleotides, as described above with respect to FIG. 4A or 4B, to form filaments whose selected final length is selected to just bridge the distance between the anchoring regions. Following self assembly, the wire may be ligated to form a continuous filament covalently bridging the two regions.

Where the filaments between substrate regions are intended to function as semiconductor or conductor wires, the filaments may be further coated with a conductive or other desired film, according to known micro- or nano-fabrication methods, such as low-angle deposition.

In another embodiment, the double-stranded nucleic acid filament may or may not be treated with a zinc, cobalt, or nickel salt under conditions effective to incorporate Zn, Co, or Ni atoms between the bases of the nucleic acid filament. U.S. Pat. Nos. 5,824,473; 6,432,641; and 6,974,703 are incorporated herein by reference.

In still another embodiment, the filaments may serve as photomask lines, allowing the substrate surface to be irradiated, to render with linear regions below the filament either susceptible or resistant to surface photoetching, as one step in a micro- or nano-fabrication process.

Figure 6:
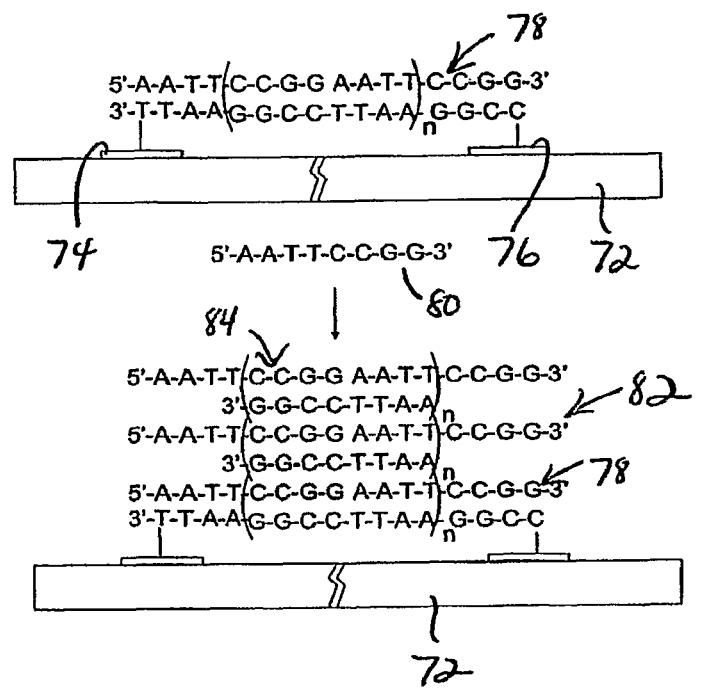
FIG. 6 shows the synthesis of bundled double-stranded polynucleotides in which one of the polynucleotides is chemically bound to a solid support.

FIG. 6 illustrates a method for forming sequence-aligned bundles of filaments, such as indicated at 82. In this method, a single, continuous double-stranded filament 78 having a known length and sequence is prepared, e.g., by solid-phase synthesis, and joined to two regions 74, 76 on a substrate 72, as shown at the top in the figure. As seen, filament 78 has the same repeating, offset-oligonucleotide sequence as that formed by self assembly of the oligonucleotides 80. When the substrate 72 and attached defined-length filament 78 is exposed to a solution of oligonucleotides 80, the latter self-assemble into additional filaments, with the self-assembly being guided by the existing filament, so that each new filament tends to adopt a sequence alignment with the existing "template" filament(s), forming a bundle of filaments, like filament 84 that are all in sequence alignment.

Although the invention has been described with reference to particular embodiments and applications, it will be appreciated that various changes and modifications may be made without departing from the claimed invention.

It is claimed:

1. A method of synthesizing a double-stranded nucleic acid filament, the method comprising:
   selecting a single species of an oligonucleotide including a first segment and a second segment wherein the first segment and the second segment:
   are of non-random sequence;
   have pre-determined lengths;
   have pre-adjusted ratios of A:T/G:C between 1% and 50%;
   forming by self-assembly under oligonucleotide hybridization conditions, a pair of substantially contiguous single strands of the double-stranded nucleic acid filament composed of multiple instances of the single species of the oligonucleotide; and
   terminating self-assembly of the double-stranded nucleic acid filament with chain terminator units, wherein the chain terminator units are composed of the nucleotides of the first segment or of the nucleotides of the second segment.

2. The method of claim 1, wherein the first segment and the second segment of the oligonucleotide are palindromic and a first length of the first segment is symmetric with a second length of the second segment.

3. The method of claim 1, wherein the first segment and the second segment of the oligonucleotide are palindromic and a first length of the first segment is asymmetric with a second length of the second segment.

4. The method of claim 1, wherein the oligonucleotide has a 5'-end phosphate group, permitting ligation of the 5'-end of one oligonucleotide in each strand to a 3'-end of an adjacent oligonucleotide in the same strand.

5. The method of claim 1, wherein the oligonucleotide contains between 1 to 3 nucleotide bases between the first segment and the second segment and each of the substantially contiguous single strands of the double-stranded nucleic acid filament contains periodic gaps that are 1 to 3 bases in length and offset from gaps in the other strand in the filament.

6. The method of claim 1, wherein the first segment of the oligonucleotide is composed substantially of A and T bases, and the second segment of the oligonucleotide is composed substantially of G and C bases, and the double stranded nuceic acid filament has regions composed substantially of paired A and T bases alternating with regions of paired G and C bases.

* * * * *